(12) United States Patent
Li (10) Patent No.: US 10,393,712 B2
(45) Date of Patent: Aug. 27, 2019

(54) SYSTEMS AND METHODS USING A GAS QUALITY SENSOR

(71) Applicant: Cummins Inc., Columbus, IN (US)

(72) Inventor: Shu Li, Columbus, IN (US)

(73) Assignee: Cummins Inc., Columbus, IN (US)

( * ) Notice: Subject to any disclaimer, the term of this patent is extended or adjusted under 35 U.S.C. 154(b) by 227 days.

(21) Appl. No.: 15/463,419

(22) Filed: Mar. 20, 2017

(65) Prior Publication Data

US 2017/0276655 A1 Sep. 28, 2017

Related U.S. Application Data

(60) Provisional application No. 62/311,597, filed on Mar. 22, 2016.

(51) Int. Cl.
*G01N 21/39* (2006.01)
*G01N 33/00* (2006.01)
*F02D 41/14* (2006.01)
*F02D 19/02* (2006.01)
*G01N 21/3504* (2014.01)
*F02D 41/00* (2006.01)

(52) U.S. Cl.
CPC ....... *G01N 33/0006* (2013.01); *F02D 19/026* (2013.01); *F02D 41/0025* (2013.01); *F02D 41/0027* (2013.01); *F02D 41/1402* (2013.01); *F02D 41/1451* (2013.01); *G01N 21/3504* (2013.01); *G01N 21/39* (2013.01); *F02D 2200/0611* (2013.01)

(58) Field of Classification Search
USPC ...................................................... 73/1.06
See application file for complete search history.

(56) References Cited

U.S. PATENT DOCUMENTS

| | | |
|---|---|---|
| 6,642,720 B2 | 11/2003 | Maylotte et al. |
| 6,947,830 B1 | 9/2005 | Froloff et al. |
| 7,127,935 B2 | 10/2006 | Bonne et al. |
| 7,266,439 B2 | 9/2007 | Wang et al. |
| 7,526,944 B2 | 5/2009 | Sabata et al. |
| 8,712,335 B2 | 4/2014 | Mathur et al. |
| 2007/0152813 A1 | 7/2007 | Mathur et al. |

(Continued)

FOREIGN PATENT DOCUMENTS

| | | |
|---|---|---|
| WO | WO 2012/150516 | 11/2012 |
| WO | WO 2013/126278 | 8/2013 |

*Primary Examiner* — Peter J Macchiarolo
*Assistant Examiner* — Mohammed E Keramet-Amircolai
(74) *Attorney, Agent, or Firm* — Foley & Lardner LLP (57) ABSTRACT

An apparatus includes an aggregation circuit and a calibration circuit. The aggregation circuit is structured to interpret fuel data indicative of a fuel composition of a fuel provided by a fuel source from a plurality of gas quality sensors. Each gas quality sensor is associated with an individual engine system. Each engine system is positioned at a respective geographic location. The calibration circuit is structured to compare the fuel data received from each of the plurality of gas quality sensors that are located within a geographic area, determine a gas quality sensor miscalibration value for the plurality of gas quality sensors within the geographic area based on the fuel data received from each of the plurality of gas quality sensors within the geographic area, and remotely calibrate a miscalibrated gas quality sensor based on the gas quality sensor miscalibration value.

20 Claims, 6 Drawing Sheets

(56) References Cited

U.S. PATENT DOCUMENTS

| | | | |
|---|---|---|---|
| 2008/0272389 A1* | 11/2008 | Rogne | G01J 3/108 257/99 |
| 2010/0002234 A1* | 1/2010 | Cormier | G01N 21/3504 356/436 |
| 2010/0219960 A1* | 9/2010 | Moe | G01N 33/0032 340/632 |
| 2013/0184908 A1* | 7/2013 | Sujan | B60W 10/02 701/22 |
| 2014/0104613 A1* | 4/2014 | Birnkrant | G01J 3/28 356/402 |
| 2014/0216129 A1* | 8/2014 | Schmidlin | G01N 33/0062 73/23.2 |
| 2014/0238032 A1 | 8/2014 | Fitzgerald et al. | |
| 2014/0358381 A1* | 12/2014 | Holland | G01N 21/55 701/50 |
| 2015/0369693 A1* | 12/2015 | Morris | G01M 3/38 356/437 |
| 2015/0373285 A1* | 12/2015 | Morris | G01N 21/274 250/252.1 |
| 2016/0153371 A1* | 6/2016 | Ge | F02D 19/0678 123/458 |

* cited by examiner

SYSTEMS AND METHODS USING A GAS QUALITY SENSOR

CROSS-REFERENCE TO RELATED PATENT APPLICATIONS

This application claims the benefit of U.S. Provisional Patent Application No. 62/311,597, filed Mar. 22, 2016, entitled "SYSTEMS AND METHODS USING A GAS QUALITY SENSOR," which is incorporated herein by reference in its entirety.

TECHNICAL FIELD

The present application relates generally to the field of gas quality sensors. More particularly, the present application relates to systems and methods using a gas quality sensor in various applications, such as power generators, vehicles, and the like.

BACKGROUND

As shale gas becomes more mainstream, fuel quality and fuel compositions are more frequently fluctuating. Such fluctuations in fuel compositions may lead to poor engine performance, which may adversely cause engine fatigue and/or damage leading to down time of the engine.

SUMMARY

One embodiment relates to an apparatus. The apparatus includes an aggregation circuit and a calibration circuit. The aggregation circuit is structured to interpret fuel data indicative of a fuel composition of a fuel acquired by a plurality of gas quality sensors. Each of the plurality of gas quality sensors is associated with an individual engine system. Each engine system is positioned at a respective geographic location having a fuel source that provides the fuel. The calibration circuit is structured to compare the fuel data received from each of the plurality of gas quality sensors that are within a geographic area, determine a gas quality sensor miscalibration value for the plurality of gas quality sensors within the geographic area based on the fuel data received from each of the plurality of gas quality sensors within the geographic area, and remotely calibrate a miscalibrated gas quality sensor based on the gas quality sensor miscalibration value.

Another embodiment relates to a method. The method includes aggregating fuel data indicative of a fuel composition of a fuel received from a plurality of fuel sensors, each of the plurality of fuel sensors associated with an individual engine system, each engine system positioned at a respective geographic location having a fuel source that provides the fuel; comparing the fuel data received from each of the plurality of fuel sensors that are located within a geographic area; determining a fuel sensor miscalibration value for the plurality of fuel sensors within the geographic area based on the fuel data received from each of the plurality of fuel sensors within the geographic area; and remotely calibrating a miscalibrated fuel sensor based on the fuel sensor miscalibration value.

Yet another embodiment relates to a system. The system includes a gas quality sensor and a controller. The gas quality sensor is positioned downstream of a fuel source and upstream of an engine of an engine system. The gas quality sensor is structured to acquire fuel data indicative of a fuel composition of a fuel provided by the fuel source to the engine. The controller is communicably and operatively coupled to the gas quality sensor and the engine. The controller is structured to receive the fuel data from the gas quality sensor and adjust operation of the engine based on the fuel data.

Still another embodiment relates to a system. The system includes a wireless sensor network and an external monitoring system. The wireless sensor network includes a plurality of gas quality sensors. Each of the plurality of gas quality sensors are associated with an engine system and positioned to acquire fuel data indicative of a fuel composition of a fuel within the engine system provided by a fuel source to an engine of the engine system. The external monitoring system is communicably coupled to each of the plurality of gas quality sensors. The external monitoring system is structured to receive the fuel data from each of the plurality of gas quality sensors, determine that at least one of the plurality of gas quality sensors is miscalibrated based on the fuel data, and remotely calibrate the at least one of the plurality of gas quality sensors that is miscalibrated.

These and other features, together with the organization and manner of operation thereof, will become apparent from the following detailed description when taken in conjunction with the accompanying drawings.

DETAILED DESCRIPTION

Following below are more detailed descriptions of various concepts related to, and implementations of, methods, apparatuses, and systems for using a gas quality sensor. The various concepts introduced above and discussed in greater detail below may be implemented in any of numerous ways, as the described concepts are not limited to any particular manner of implementation. Examples of specific implementations and applications are provided primarily for illustrative purposes.

Referring to the figures generally, systems, apparatuses, and methods are shown of engine systems using a gas quality sensor. As shale gas becomes mainstream, fluctuations in gas quality are becoming more evident, even for pipeline natural gas. Such fluctuation in gas compositions may lead to poor engine performance such as engine knock and/or engine shutdown, which may adversely cause engine fatigue and/or damage leading to down time. Traditional systems may use a standard gas chromatograph approach, which is accurate in determining fuel composition, however is relatively slow in making these determinations and thus does not provide adequate feed forward control for engines controllers to appropriately respond to the gas quality fluctuations.

The systems, apparatuses, and methods of the present disclosure may additionally or alternatively include a gas quality sensor (GQS) to assist in providing robust, fuel flexible engines systems. A fast and adaptable GQS may increase fuel flexibility of engines in both test cells and in the field by enabling early warning and feed forward control to engines systems including the GQS through wired and/or wireless communication. The GQS of the proposed systems, apparatuses, and methods may reduce engine down time at minimal additional cost through quick feed forward control, may facilitate remote data analytics (e.g., a wireless sensor network (WSN), etc.), and/or may facilitate remote calibration of engine systems and/or the GQS itself. A WSN of GQSs may be used to perform a worldwide gas quality survey (e.g., gas quality trend analyses, etc.), while at the same time improve sensor functionalities to improve engine performance through cloud based calibrations. Thus, the WSN may draw data from the remote server based on geographic location, to get an idea of a range of fuel compositions around the same geographic location and help calibrate the respective GQS.

Figure 1:
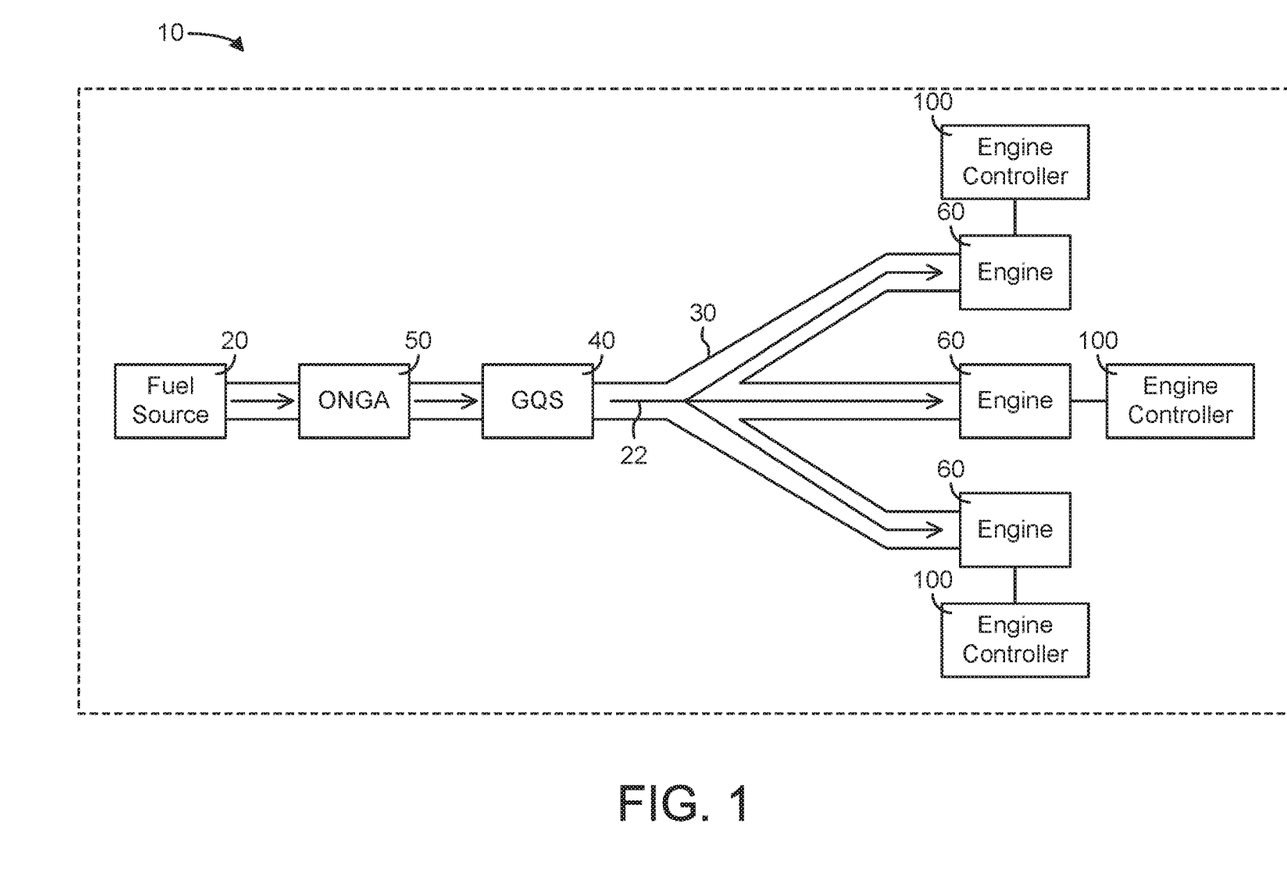
FIG. 1 is a schematic diagram of an engine system, according to an example embodiment.

Referring now to FIG. 1, a schematic diagram of an engine system 10 is shown according to an example embodiment. According to one embodiment, the engine system 10 is structured as a stationary engine system (e.g., a stationary power generation system, a test cell center, etc.). In the example shown, the engine system 10 is a test cell environment having one or more engines 60. The one or more engines 60 may be used in a vehicle application (e.g., a vehicle such as an on-road or an off-road vehicle including, but not limited to, line-haul trucks, mid-range trucks, cars, boats, tanks, airplanes, and any other type of vehicle that utilizes a gas quality sensor, etc.) or a stationary application.

As shown in FIG. 1, the engine system 10 includes a fuel source 20 in fluid communication with at least one engine 60 via a conduit or main line (e.g., pipeline, fuel line, etc.), shown as fuel line 30. In one embodiment, the engine system 10 includes a plurality of engines 60 (e.g., two, three, ten, etc.; a test cell center having at least one engine 60; etc.). In other embodiments, the engine system 10 includes one engine 60. The fuel line 30 is structured to provide a fuel, shown as fuel 22, from the fuel source 20 to the engines 60. In one embodiment, the fuel source 20 includes a well head such that the fuel 22 (e.g., natural gas, etc.) is pulled directly from a well to operate the engines 60. In another embodiment, the fuel source 20 includes a reservoir or tank structured to store the fuel 22 (e.g., natural gas, gasoline, diesel, propane, etc.) to operate the engines 60.

According to one embodiment, the engines 60 are structured as a spark-ignition internal combustion engines that utilize natural gas. However, in various alternate embodiments, the engines 60 may be structured as any type of engine (e.g., spark-ignition, compression-ignition, etc.) that utilizes any type of fuel (e.g., gasoline, diesel, propane, ethanol, etc.). Within the engines 60, air from the atmosphere is combined with the fuel 22, and combusted, to power the engines 60. Combustion of the fuel 22 and air in the compression chambers of the engine 60 produces exhaust gas that is operatively vented to an exhaust manifold and/or to an exhaust aftertreatment system.

As shown in FIG. 1, each of the engines 60 includes a controller, shown as engine controllers 100. The engine controllers 100 may be structured to control operation of the engines 60 based on a fuel composition of the fuel 22 from the fuel source 20. The engine controllers 100 may be communicably coupled to various sensors to receive fuel data indicative of the fuel composition of the fuel 22, as is described more fully herein. In an alternative embodiment, the engines 60 of the engine system 10 are communicably coupled to a single, central engine controller 100 structured to control the operation of each of the engines 60 of the engine system 10.

As shown in FIG. 1, the engine system 10 includes a first fuel sensor, shown as gas quality sensor (GQS) 40. According to one embodiment, a single GQS 40 is positioned along the fuel line 30 between the fuel source 20 and the engines 60. The GQS 40 may be structured to acquire first fuel data indicative of a fuel composition of the fuel 22 flowing along the fuel line 30 from the fuel source 20. In other embodiments, a plurality of GQSs 40 are positioned along the fuel line 30 between the fuel source 20 and the engines 60. For example, a GQS 40 may be positioned along the fuel line 30 proximate each of the engine 60 (e.g., just upstream of a fuel intake of the engines 60, etc.). The GQSs 40 may thereby be structured to acquire first fuel data indicative of a fuel composition of the fuel 22 entering each of the engines 60. According to an example embodiment, the GQS 40 is or includes an optical sensor structured to acquire the first fuel data indicative of the fuel composition of the fuel 22 flowing along the fuel line 30 from the fuel source 20. In some embodiments, the optical sensor is or includes a non-dispersive infrared (NDIR) optical sensor. In some embodiments, the optical sensor is or includes a tunable diode laser (TDL) optical sensor. In still other embodiments, the optical sensor is or includes another type of optical sensor (e.g., a Fourier transform infrared (FTIR) optical sensor, etc.). According to another example embodiment, the GQS 40 is or includes another type of sensor structured to acquire the first fuel data indicative of the fuel composition of the fuel 22. For example, the GQS 40 may include a sensor that uses sensing principles other than optics including, but not limited to, ultrasonic, thermal conductivity, photoacoustics, and/or electrochemical.

In some embodiments, as shown in FIG. 1, the engine system 10 further includes a second fuel sensor, shown as online natural gas analyzer (ONGA) 50. According to one embodiment, a single ONGA 50 is positioned along the fuel line 30 between the fuel source 20 and the engines 60. In one embodiment, the ONGA 50 is positioned upstream of the GQS 40. In another embodiment, the ONGA 50 is positioned downstream of the GQS 40. The ONGA 50 may be structured to acquire second fuel data indicative of a fuel composition of the fuel 22 flowing along the fuel line 30 from the fuel source 20. In other embodiments, a plurality of ONGAs 50 are positioned along the fuel line 30 between the fuel source 20 and the engines 60. For example, an ONGA 50 may be positioned along the fuel line 30 proximate each of the engine 60 (e.g., just upstream of a fuel intake of the engines 60, etc.). The ONGAs 50 may thereby be structured to acquire second fuel data indicative of a fuel composition of the fuel 22 entering each of the engines 60. According to an example embodiment, the ONGA 50 is structured to utilize a gas chromatograph approach to determine the fuel composition of the fuel 22 flowing along the fuel line 30 from the fuel source 20.

According to an example embodiment, the GQS 40 is capable of acquiring the first fuel data to determine the fuel composition of the fuel 22 relatively quickly (e.g., every couple seconds, relative to the ONGA 50, etc.), while the ONGA 50 is capable of acquiring the second fuel data to determine the fuel composition of the fuel 22 relatively more accurately, but at a slower speed (e.g., every fifteen minutes, etc.). Therefore, an engine system 10 including both the GQS 40 and the ONGA 50 may provide quality assurance (e.g., given the accuracy of the ONGA 50, etc.), as well as fast response time for feed forward control (e.g., via the GQS 40, etc.) for combustion control within the engines 60 by the engine controllers 100. The GQS 40 may thereby provide an early warning capability regarding fuel quality and composition fluctuations to avoid incidents such as poor engine performance including engine knock and/or engine shutdown (e.g., which may adversely cause engine fatigue and/or damage leading to down time, etc.). The GQS 40 and/or the ONGA 50 may thereby be communicably coupled to the engine controllers 100 to facilitate transmitting the first fuel data and/or the second fuel data to the engine controllers 100 for control purposes to avoid such incidents. In some embodiments, the GQS 40 and/or the ONGA 50 may include communication circuitry structured to facilitate the exchange of information, data, values, non-transient signals, etc. between and among the engine controllers 100 and an external system (e.g., global analytics system 250, etc.). Communication with the external system may facilitate remote monitoring of the engine system 10 (e.g., the fuel composition of the fuel 22, etc.) and/or remote calibration of the GQS 40 and/or the ONGA 50.

The engine controllers 100 may be structured to control the operation of the engines 60 and associated components, such as the GQS 40 and/or the ONGA 50. Communication between and among the components of the engine system 10 may be via any number of wired or wireless connections (e.g., any standard under IEEE 802, etc.). For example, a wired connection may include a serial cable, a fiber optic cable, a CAT5 cable, or any other form of wired connection. In comparison, a wireless connection may include the Internet, Wi-Fi, cellular, Bluetooth, ZigBee, radio, etc. In one embodiment, a controller area network (CAN) bus provides the exchange of signals, information, and/or data. The CAN bus can include any number of wired and wireless connections that provide the exchange of signals, information, and/or data. The CAN bus may include a local area network (LAN), or a wide area network (WAN), or the connection may be made to an external computer (for example, through the Internet using an Internet Service Provider).

Because the engine controllers 100 are communicably coupled to the systems and components of FIG. 1, the engine controllers 100 may be structured to receive data from one or more of the components shown in FIG. 1. For example, the data may include the first fuel data (e.g., acquired by the GQS, etc.), the second fuel data (e.g., acquired by the ONGA 50, etc.), and/or engine operation data (e.g., acquired by one or more engine sensors, etc.). As the components of FIG. 1 are shown to be embodied in the engine system 10, in one embodiment the engine controllers 100 may be embodied as an electronic control unit (ECU) or an add-on to an ECU. In some embodiments, the engine controllers 100 may be a stand-alone tool that performs all required data logging, data tracking, data analysis, etc. needed to determine the quality of the fuel 22 and/or control the engines 60. In some embodiments, the engine controllers 100 are included in the ECU of the engines 60. In an alternative embodiment, the engine controllers 100 are web based, server based, and/or application based (e.g., a smartphone app, a controller on the internet, etc.). The structure and function of the engine controllers 100 are further described in regard to FIG. 2.

Figure 2:
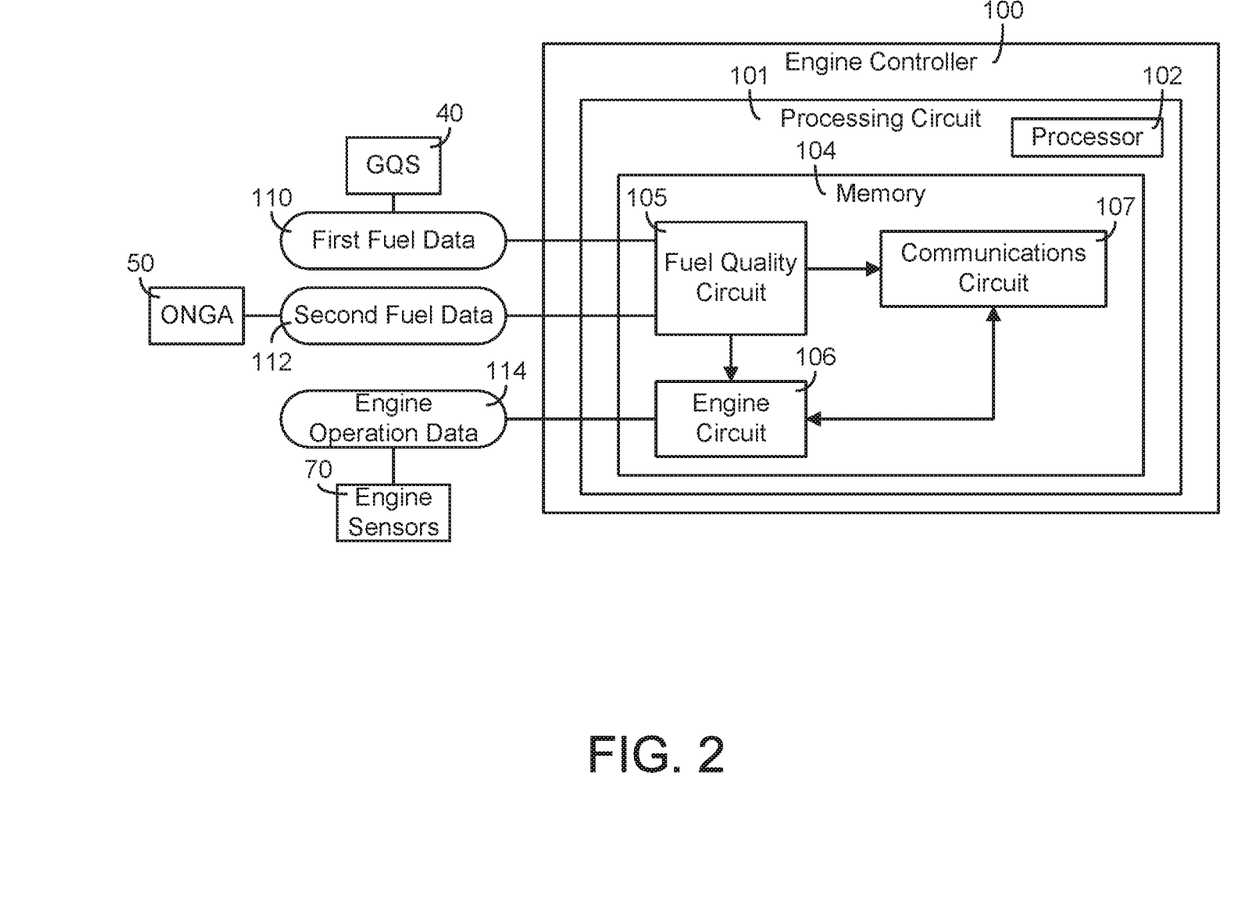
FIG. 2 is a schematic diagram of a controller of an engine of the engine system of FIG. 1, according to an example embodiment.

Referring now to FIG. 2, the function and structure of the engine controllers 100 are shown according to an example embodiment. The engine controllers 100 are shown to include a processing circuit 101 including a processor 102 and a memory 104. The processor 102 may be implemented as a general-purpose processor, an application specific integrated circuit (ASIC), one or more field programmable gate arrays (FPGAs), a digital signal processor (DSP), a group of processing components, or other suitable electronic processing components. The one or more memory devices 104 (e.g., NVRAM, RAM, ROM, Flash Memory, hard disk storage, etc.) may store data and/or computer code for facilitating the various processes described herein. Thus, the one or more memory devices 104 may be communicably connected to the processor 102 and provide computer code or instructions to the processor 102 for executing the processes described in regard to the engine controllers 100 herein. Moreover, the one or more memory devices 104 may be or include tangible, non-transient volatile memory or non-volatile memory. Accordingly, the one or more memory devices 104 may include database components, object code components, script components, or any other type of information structure for supporting the various activities and information structures described herein.

The memory 104 is shown to include various circuits for completing the activities described herein. More particularly, the memory 104 includes a fuel quality circuit 105, an engine circuit 106, and a communications circuit 107. The circuits 105-107 are structured to receive and interpret various data (e.g., fuel data, etc.) for feed forward control to adjust operation of the engines 60 based on the data. While various circuits with particular functionality are shown in FIG. 2, it should be understood that the engine controllers 100 and memory 104 may include any number of circuits for completing the functions described herein. For example, the activities of multiple circuits may be combined as a single circuit, as additional circuits with additional functionality may be included, etc. Further, it should be understood that the engine controllers 100 may further control other activity beyond the scope of the present disclosure.

Certain operations of the engine controllers 100 described herein include operations to interpret and/or to determine one or more parameters. Interpreting or determining, as utilized herein, includes receiving values by any method known in the art, including at least receiving values from a datalink or network communication, receiving an electronic signal (e.g., a voltage, frequency, current, or PWM signal) indicative of the value, receiving a computer generated parameter indicative of the value, reading the value from a memory location on a non-transient computer readable storage medium, receiving the value as a run-time parameter by any means known in the art, and/or by receiving a value by which the interpreted parameter can be calculated, and/or by referencing a default value that is interpreted to be the parameter value.

The fuel quality circuit 105 may include or be operatively and communicably coupled to the GQS 40 and/or the ONGA 50 to receive at least one of first fuel data 110 from the QGS 40 and second fuel data 112 from the ONGA 50. The first fuel data 110 and/or the second fuel data 112 may be indicative of the fuel composition of the fuel 22 at, at least one of, (i) flowing along the fuel line 30 from the fuel source 20 and (ii) entering each respective engine 60. The fuel quality circuit 105 may be structured to interpret at least one of the first fuel data 110 and the second fuel data 112 to monitor the quality of the fuel 22 and/or fluctuations, changes, and/or abnormalities in the fuel composition of the fuel 22 being received by the engines 60. The fuel quality circuit 105 may be further structured to store the first fuel data 110 and/or the second fuel data 112 to create a history of and/or track the fuel composition of the fuel 22 from the fuel source 20 over the lifetime of the engine system 10 and/or fuel source 20. The fuel quality circuit 105 may be further structured to store the first fuel data 110 and/or the second fuel data 112 and/or the determinations made (e.g., regarding the fluctuations, changes, and/or abnormalities in the fuel composition, etc.) for later use by another circuit (e.g., the engine circuit 106, the communications circuit 107, etc.) of the engine controller 100 and/or another system (e.g., a remote system, a global analytics system, transmitted by the communications circuit 107, etc.).

According to one embodiment, the fuel quality circuit 105 may include communication circuitry structured to facilitate the exchange of information, data, values, non-transient signals, etc. between and among the fuel quality circuit 105, the GQS 40, the ONGA 50, the engine circuit 106, and/or the communications circuit 107. For example, the communication circuitry may include a channel comprising any type of communication channel (e.g., fiber optics, wired, wireless, etc.), wherein the channel may include any additional component for signal enhancement, modulation, demodulation, filtering, and the like. In this regard, the fuel quality circuit 105 may include communication circuitry including, but not limited to, wired and wireless communication protocol to facilitate reception of the first fuel data 110 and/or the second fuel data 112.

In another embodiment, the fuel quality circuit 105 may include machine-readable media stored by the memory 104 and executable by the processor 102, wherein the machine-readable media facilitates performance of certain operations to receive the first fuel data 110 and/or the second fuel data 112. For example, the machine-readable media may provide an instruction (e.g., command, etc.) to the GQS 40 and/or the ONGA 50 to acquire the first fuel data 110 and/or the second fuel data 112. In this regard, the machine-readable media may include programmable logic that defines the frequency of acquisition of the first fuel data 110 and/or the second fuel data 112. In yet another embodiment, the fuel quality circuit 105 may include any combination of machine-readable content, communication circuitry, the GQS 40, and the ONGA 50.

The engine circuit 106 may be structured to receive engine operation data 114 indicative of at least one operating characteristic of the engine 60. The engine circuit 106 may include or be operatively and communicably coupled to engine sensors 70 structured to acquire the engine operation data 114. The at least one engine characteristic may include an engine speed, an engine temperature, a throttle position, an amount of fueling, a power output, an ignition timing, a fuel injection timing, a combustion temperature, a power output, a torque output, and/or any other engine characteristics that indicate a current operating parameter or a current demand required to be met by the engine 60. In some embodiments, the engine circuit 106 may include or be communicably and operatively coupled to one or more of the engines 60 as a means for controlling operation of the engine 60.

The engine circuit 106 may be further structured to receive the first fuel data 110, the second fuel data 112, and/or the determinations made by the fuel quality circuit 105 for feed forward control of the engine 60. The engine circuit 106 may be structured to adjust the at least one operating characteristic of the engine 60 (e.g., engine speed, ignition timing, fuel injection timing, etc.) based on the first fuel data 110, the second fuel data 112, and/or the engine operation data 114. For example, the first fuel data 110 and/or the second fuel data 112 may indicate that the fuel composition of the fuel 22 is changing and may cause engine knock based on the current operating characteristics of the engine 60 indicated by the engine operation data 114. The engine circuit 106 may thereby be structured to adjust the operation of the engine 60 to compensate for the fluctuations in fuel composition to maintain operation of the engine 60 at optimal conditions or performance. Such feed forward control may also limit or reduce harmful engine operation (e.g., knock, etc.) such that engine downtime and progressive damage are mitigated or minimized. The engine circuit 106 may be further structured to store the engine operation data 114 for later use by another circuit (e.g., the communications circuit 107, etc.) of the engine controller 100 and/or another system (e.g., a remote system, a global analytics system, transmitted via the communications circuit 107, etc.).

According to one embodiment, the engine circuit 106 may include communication circuitry structured to facilitate the exchange of information, data, values, non-transient signals, etc. between and among the engine circuit 106, the engine sensors 70, the fuel quality circuit 105, and/or the communications circuit 107. For example, the communication circuitry may include a channel comprising any type of communication channel (e.g., fiber optics, wired, wireless, etc.), wherein the channel may include any additional component for signal enhancement, modulation, demodulation, filtering, and the like. In this regard, the engine circuit 106 may include communication circuitry including, but not limited to, wired and wireless communication protocol to facilitate reception of the first fuel data 110, the second fuel data 112, and/or the engine operation data 114.

In another embodiment, the engine circuit 106 may include machine-readable media stored by the memory 104 and executable by the processor 102, wherein the machine-readable media facilitates performance of certain operations to receive the first fuel data 110, the second fuel data 112, and/or the engine operation data 114. For example, the machine-readable media may provide an instruction (e.g., command, etc.) to the GQS 40, the ONGA 50, and/or the engine sensors 70 to acquire the first fuel data 110, the second fuel data 112, and/or the engine operation data 114. In this regard, the machine-readable media may include programmable logic that defines the frequency of acquisition of the first fuel data 110, the second fuel data 112, and/or the engine operation data 114. In yet another embodiment, the engine circuit 106 may include any combination of machine-readable content, communication circuitry, the engine(s) 60, and the engine sensors 70.

The communications circuit 107 may be structured to communicate with an external system or server (e.g., a remote system, a global analytics system 250, etc.). In one embodiment, the communications circuit 107 transmits the first fuel data 110, the second fuel data 112, and/or the engine operation data 114 regarding the fuel composition of the fuel 22 and/or the engine operating characteristics to the external system for further processing and analysis. The communications circuit 107 may thereby facilitate the remote calibration of at least one of the engine controller 100, the GQS 40, and the ONGA 50. In another embodiment, the communications circuit 107 only transmits the engine operation data 114 to the external system or server, and the GQS 40 and/or the ONGA 50 directly transmit the first fuel data 110 and/or the second fuel data 112 to the external system. The communications circuit 107 may thereby facilitate the remote calibration of the engine controller 100 and the external system may have the capability to directly remotely calibrate the GQS 40 and/or the ONGA 50.

According to one embodiment, the communications circuit 107 may include communication circuitry structured to facilitate the exchange of information, data, values, non-transient signals, etc. between and among the communications circuit 107, the engine circuit 106, the fuel quality circuit 105, the GQS 40, the ONGA 50, and/or the external system. For example, the communication circuitry may include a channel comprising any type of communication channel (e.g., fiber optics, wired, wireless, etc.), wherein the channel may include any additional component for signal enhancement, modulation, demodulation, filtering, and the like. In this regard, the communications circuit 107 may include communication circuitry including, but not limited to, wired and wireless communication protocol to facilitate reception and transmission of the first fuel data 110, the second fuel data 112, and/or the engine operation data 114.

Figure 3:
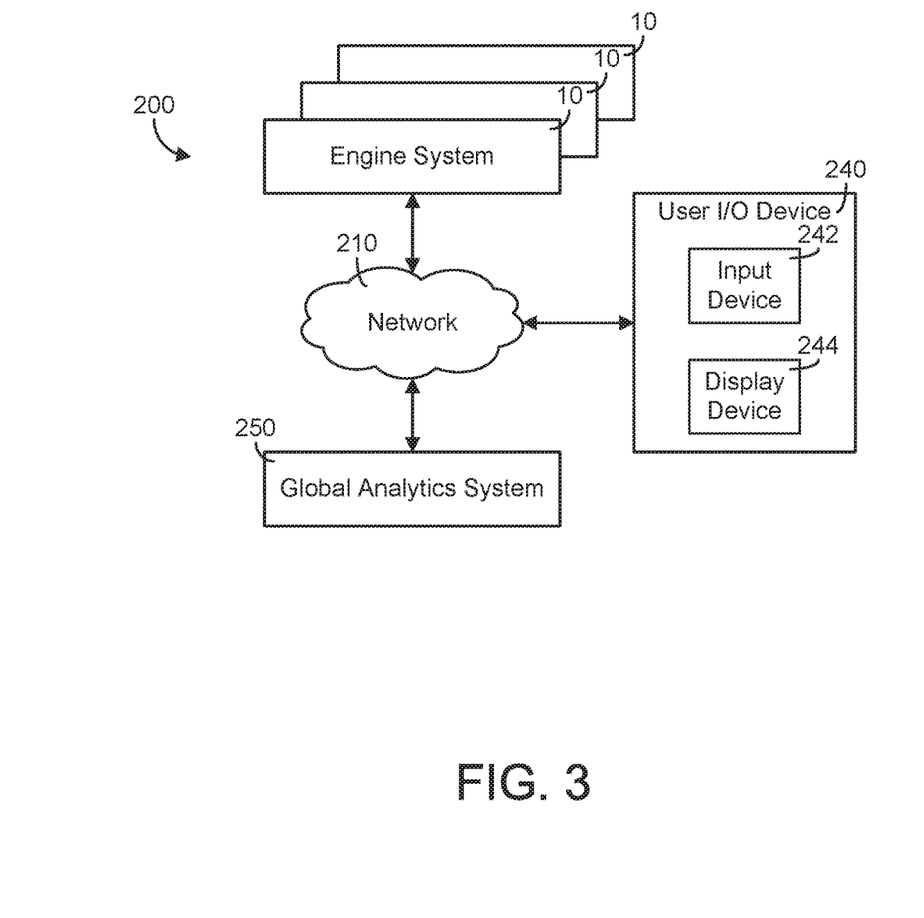
FIG. 3 is a schematic diagram of a network system communicably coupling engine systems to an external system and a user input/output device, according to an example embodiment.

Referring now to FIG. 3, a schematic diagram of a monitoring system 200 is shown according to one embodiment. As shown in FIG. 3, the monitoring system 200 includes a plurality of engine systems 10 communicably coupled over a network 210 to an external system, shown as global analytics system 250. The monitoring system 200 may also include a user input/output (I/O) device 240 communicably coupled to the global analytics system 250 either over the network 210 or directly coupled (e.g., via a wired connection, etc.). The global analytics system 250 may be structured to facilitate remote monitoring, trend analysis, and/or remote calibration of one or more components of each of the engine systems 10 (e.g., the GQS 40, the ONGA 50, the engine controllers 100, the engines 60, etc.). The global analytics system 250 may be accessed by a web interface (e.g., a website, etc.) and/or an application interface (e.g., a smartphone, tablet, computer application, etc.) via the user I/O device 240. In some embodiments, the global analytics system 250 may send notifications directly to an owner of the engine systems 10 (e.g., via an email, a push notification, a text message, etc.).

The network 210 may be any type of communication protocol that facilitates the exchange of information between and among the global analytics system 250, the engine systems 10 (e.g., the GQS 40, the ONGA 50, the engine controllers 100, etc.), and/or the user I/O device 240. In this regard, the communication protocol may include any type and number of wired and wireless protocols (e.g., any standard under IEEE 802, etc.). For example, a wired connection may include a serial cable, a fiber optic cable, a CAT5 cable, or any other form of wired connection. In comparison, a wireless connection may include the Internet, Wi-Fi, Bluetooth, Zigbee, cellular, radio, etc. In one embodiment, a controller area network (CAN) bus including any number of wired and wireless connections that provide the exchange of signals, information, and/or data. Further, the network 210 may include a local area network (LAN) or a wide area network (WAN), or the connection may be made to an external computer (for example, through the Internet using an Internet Service Provider).

In one embodiment, the engine systems 10 represent the engine systems 10 owned and/or operated by a user (e.g., a customer, a fleet manager, etc.) of the monitoring system 200. A user of monitoring system 200 may have any number of engine systems 10 (e.g., 1, 2, 3, 100, etc.). In another embodiment, the engine systems 10 represent the engine systems owned and/or operated by a plurality of users of the monitoring system 200 (e.g., a compilation of all engine systems 10 associated with the monitoring system 200, etc.). The monitoring system 200 may be structured to segregate data by customer, user, and/or engine system 10 (e.g., Customer A may only see data associated with Customer A's engine systems 10, etc.). The monitoring system 200 may be structured to also segregate data of an individual user based on access permissions (e.g., a regional manager only has access to data regarding the engine systems 10 in his/her region, etc.). The monitoring system 200 may also be structured to allow administrative rights to a user (e.g., a "super-user", etc.) such that the user is able to see all the data for all the engine systems 10.

The user I/O device 240 enables a user of the monitoring system 200 to communicate with the monitoring system 200, and more specifically the global analytics system 250 and/or the engine systems 10. In some embodiments, the user I/O device 240 is communicably coupled to the global analytics system 250 and/or the engine systems 10 via the network 210 (e.g., remotely, wirelessly, etc.). In some embodiments, the user I/O device 240 is directly communicably coupled to the global analytics system 250 and/or the engine systems 10 (e.g., with a wired connection, etc.). The user I/O device 240 may include an input device 242 and a display device 244. The input device 242 may include, but is not limited to, a keyboard, a mouse, a touchscreen device, one or more buttons and switches, voice command receivers, etc. The display device 244 is structured to provide a graphical user interface (GUI) to the user of the monitoring system 200. The display device 244 may include, but is not limited to, a touchscreen display, a projector and projection screen, a monitor or television (e.g., a LCD, LED, CRT, plasma, DLP, etc.), augmented reality glasses, a portable device (e.g., a smartphone, tablet, laptop, etc.), and/or any other known display devices that can provide a GUI. According to an example embodiment, the input device 242 enables a user to provide an input to the monitoring system 200. The input may include a display request including various configurable options for providing the GUI in a desired graphical format and/or a calibration command (e.g., of the GQS 40, the ONGA 50, the engine controllers 100, etc.). The desired graphical format may present the first fuel data 110, the second fuel data 112, the engine operation data 114, and/or other features (e.g., calibration notifications, calibration options, etc.) for one or more of the engine systems 10.

According to one embodiment, the GQSs 40, the ONGAs 50, and/or the engine sensors 70 of the engine systems 10 form a sensor network (e.g., a wireless sensor network (WSN), etc.) structured to transmit the first fuel data 110, the second fuel data 112, and/or the engine operation data 114 to the global analytics system 250 over the network 210. Each sensor may be associated with a specific geographic location and/or engine system 10.

Figure 4:
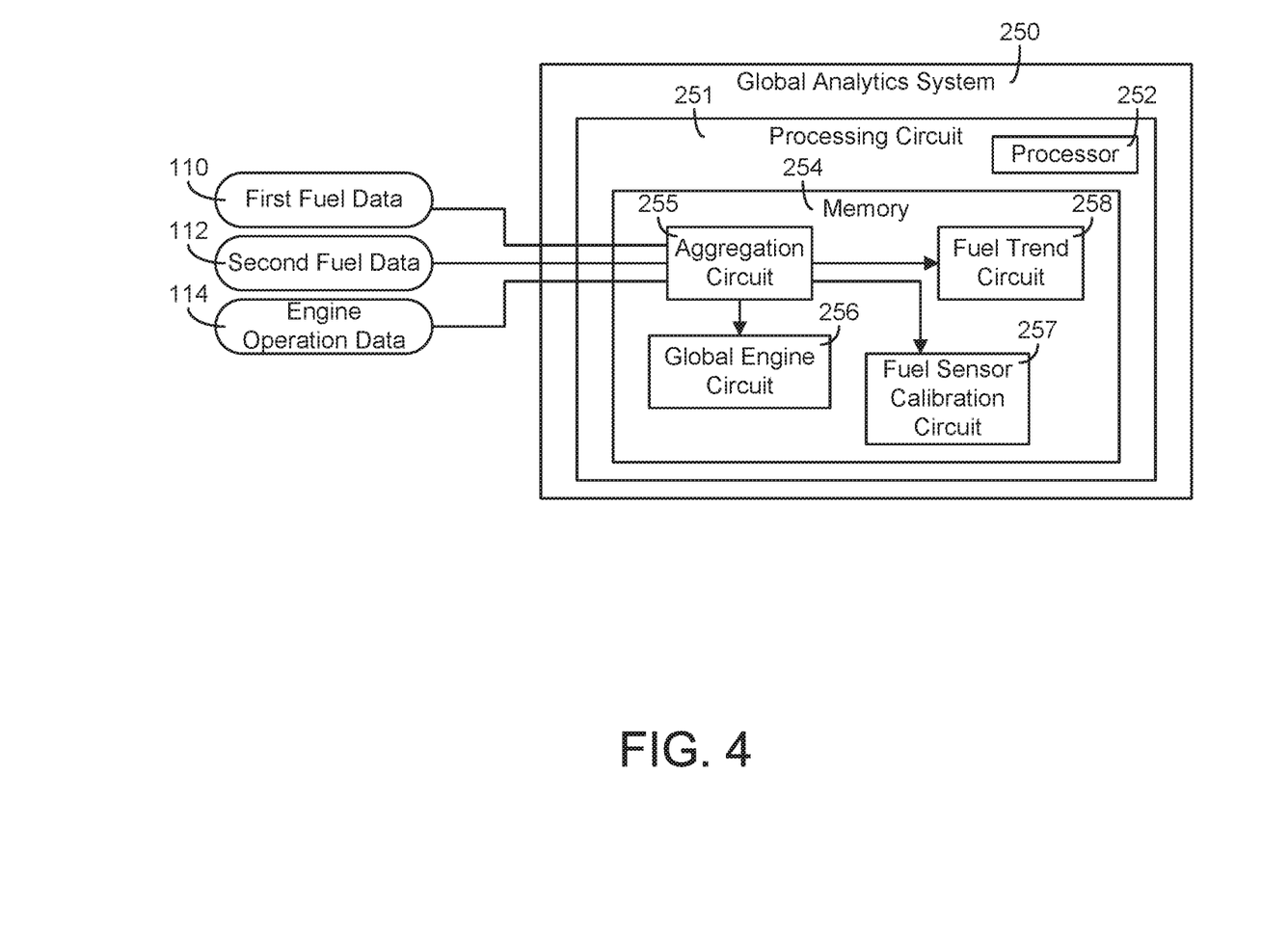
FIG. 4 is schematic diagram of the external system of FIG. 3, according to an example embodiment.

As shown in FIG. 4, the global analytics system 250 is shown to include a processing circuit 251 including a processor 252 and a memory 254. The processor 252 may be implemented as a general-purpose processor, an application specific integrated circuit (ASIC), one or more field programmable gate arrays (FPGAs), a digital signal processor (DSP), a group of processing components, or other suitable electronic processing components. The one or more memory devices 154 (e.g., NVRAM, RAM, ROM, Flash Memory, hard disk storage, etc.) may store data and/or computer code for facilitating the various processes described herein. Thus, the one or more memory devices 254 may be communicably connected to the processor 252 and provide computer code or instructions to the processor 252 for executing the processes described in regard to the global analytics system 250 herein. Moreover, the one or more memory devices 254 may be or include tangible, non-transient volatile memory or non-volatile memory. Accordingly, the one or more memory devices 254 may include database components, object code components, script components, or any other type of information structure for supporting the various activities and information structures described herein.

The memory 254 is shown to include various circuits for completing the activities described herein. More particularly, the memory 254 includes an aggregation circuit 255, a global engine circuit 256, a fuel sensor calibration circuit 257, and a fuel trend circuit 258. The circuits 255-258 are structured to receive and interpret various information and/or data (e.g., the first fuel data 110, the second fuel data 112, the engine operation data 114, etc.) to facilitate at least one of remotely monitoring each of the engine systems 10, analyzing trends of the fuel composition of the fuel 22 across each of the engine systems 10, and remotely calibrating the GQS 40, the ONGA 50, and/or the engine controllers 100 of each of the engine systems 10. While various circuits with particular functionality are shown in FIG. 4, it should be understood that the global analytics system 250 and memory 254 may include any number of circuits for completing the functions described herein. For example, the activities of multiple circuits may be combined as a single circuit, as additional circuits with additional functionality may be included, etc. Further, it should be understood that the global analytics system 250 may further control other activity beyond the scope of the present disclosure.

Certain operations of the global analytics system 250 described herein include operations to interpret and/or to determine one or more parameters. Interpreting or determining, as utilized herein, includes receiving values by any method known in the art, including at least receiving values from a datalink or network communication, receiving an electronic signal (e.g., a voltage, frequency, current, or PWM signal) indicative of the value, receiving a computer generated parameter indicative of the value, reading the value from a memory location on a non-transient computer readable storage medium, receiving the value as a run-time parameter by any means known in the art, and/or by receiving a value by which the interpreted parameter can be calculated, and/or by referencing a default value that is interpreted to be the parameter value.

The aggregation circuit 255 may be communicably coupled to one or more components of the engine systems 10 (e.g., the GQS 40, the ONGA 50, the engine controllers 100, etc.) over the network 210. According to an example embodiment, the aggregation circuit 255 is structured to receive at least one of the first fuel data 110 (e.g., from the GQSs 40, from the engine controllers 100, etc.), the second fuel data 112 (e.g., from the ONGAs 50, from the engine controllers 100, etc.), and the engine operation data 114 (e.g., from the engine controllers 100, etc.). The aggregation circuit 255 may be further structured to store the various data for later use by another circuit (e.g., the global engine circuit 256, the fuel sensor calibration circuit 257, the fuel trend circuit 258, etc.) of the global analytics system 250. In some embodiments, the aggregation circuit 255 is structured to separate the first fuel data 110, the second fuel data 112, and/or the engine operation data 114 based on the geographic location of the engine systems 10. For example, all the data from one geographic area may be isolated from the data from a second geographic area. The geographic area may be user defined or predefined within the memory 254.

According to one embodiment, the aggregation circuit 255 may include communication circuitry structured to facilitate the exchange of information, data, values, non-transient signals, etc. between and among the aggregation circuit 255, the engine systems 10 (e.g., the GQSs 40, the ONGAs 50, the engine controllers 100, etc.), the global engine circuit 256, the fuel sensor calibration circuit 257, and/or the fuel trend circuit 258. For example, the communication circuitry may include a channel comprising any type of communication channel (e.g., fiber optics, wired, wireless, etc.), wherein the channel may include any additional component for signal enhancement, modulation, demodulation, filtering, and the like. In this regard, the aggregation circuit 255 may include communication circuitry including, but not limited to, wired and wireless communication protocols to facilitate reception of the first fuel data 110, the second fuel data 112, and/or the engine operation data 114.

In another embodiment, the aggregation circuit 255 may include machine-readable media stored by the memory 254 and executable by the processor 252, wherein the machine-readable media facilitates performance of certain operations to receive the first fuel data 110, the second fuel data 112, and/or the engine operation data 114. For example, the machine-readable media may provide an instruction (e.g., command, etc.) to the network 210 operatively coupled to the engine systems 10 to monitor and acquire the first fuel data 110, the second fuel data 112, and/or the engine operation data 114. In this regard, the machine-readable media may include programmable logic that defines the frequency of acquisition of the first fuel data 110, the second fuel data 112, and/or the engine operation data 114. In yet another embodiment, the aggregation circuit 255 may include any combination of machine-readable content and communication circuitry.

The global engine circuit 256 may be structured to receive the engine operation data 114 indicative of the operating characteristics of each of the engines 60 of the engine systems 10. The global engine circuit 256 may be further structured to store the engine operation data 114 to facilitate monitoring the performance of the engine systems 10 over time. The global engine circuit 256 may be further structured to facilitate transmitting a program or logic update (e.g., a TRIMs update, a remote calibration, etc.) and/or upgrade to each of the engine controllers 100.

According to one embodiment, the global engine circuit 256 may include communication circuitry structured to facilitate the exchange of information, data, values, non-transient signals, etc. between and among the global engine circuit 256, the aggregation circuit 255, the engine systems 10 (e.g., the engine controllers 100, etc.), and/or the user I/O device 240. For example, the communication circuitry may include a channel comprising any type of communication channel (e.g., fiber optics, wired, wireless, etc.), wherein the channel may include any additional component for signal enhancement, modulation, demodulation, filtering, and the like. In this regard, the global engine circuit 256 may include communication circuitry including, but not limited to, wired and wireless communication protocols to facilitate reception of the engine operation data 114 and to transmit the updates to the engine controllers 100.

The fuel sensor calibration circuit 257 may be structured to receive the first fuel data 110 and/or the second fuel data 112 to facilitate remote calibration of the GQSs 40 and/or the ONGAs 50. In one embodiment, the fuel sensor calibration circuit 257 is structured to interpret the first fuel data 110 acquired by a plurality of GQSs 40 to determine which of the GQSs 40 may require calibration. In other embodiments, the fuel sensor calibration circuit 257 is structured to interpret the first fuel data 110 acquired by a plurality of GQSs 40 and the second fuel data 112 acquired by a plurality of ONGAs 50 to determine which of the GQSs 40 may require calibration. In yet another embodiment, the fuel sensor calibration circuit 275 is structured to interpret the engine operation data 114 acquired by the engine sensors 70 to determine which of the GQSs 40 may require calibration. As used herein, the term "miscalibrated" may refer to the GQSs 40 and/or the ONGAs 50 acquiring data that is incorrect, shifted, the wrong magnitude, above a threshold, below a threshold, off by a percentage, and/or the like such that the data facilitates poor feed forward control by the engine controllers 100. Further, the term "calibrate" as used herein may refer to correcting, adjusting, shifting, fixing, setting, etc. the GQSs 40 and/or the ONGAs 50 such that the data acquired by the GQSs 40 and/or the ONGAs 50 is of greater accuracy and/or precision.

According to one embodiment, the fuel sensor calibration circuit 257 is structured to compare the first fuel data 110 received from each of the plurality of GQSs 40 within a geographic area. For example, the geographic area may be defined by a radius (e.g., the engine systems 10 within a one, five, ten, fifty, etc. mile radius of each other, etc.). In another example, the geographic area may be defined to include the engine systems 10 where the fuel sources 20 receive fuel from the same central location (e.g., well heads that receive the fuel 22 from the same underground supply of natural gas, fuel sources 20 or reservoirs that were filled with fuel 22 from a common location or fuel processing facility, etc.).

The fuel sensor calibration circuit 257 may be further structured to determine that at least one of the GQSs 40 within the geographic area is miscalibrated based on the comparison of the first fuel data 110 received from each of the GQSs 40 within the geographic area. The fuel sensor calibration circuit 257 may determine a GQS miscalibration value based on the first fuel data 110 received from the GQSs 40 within the geographic area. For example, if the first fuel data 110 from one GQS 40 within a geographic area indicates a first fuel composition of the fuel 22 with certain constituent percentages and the first fuel data 110 from all of the other GQSs 40 within the same geographic area indicate a second fuel composition of the fuel 22 with different constituent percentages (e.g., greater than a threshold magnitude difference, greater than a threshold percentage difference, below the GQS miscalibration value, above the GQS miscalibration value, etc.) may indicate that the GQS 40 is miscalibrated. The fuel sensor calibration circuit 257 may be further structured to remotely calibrate the miscalibrated GQS 40 based on the first fuel data 110 received from each of the other GQSs 40 within the geographic area of the miscalibrated GQS 40 (e.g., calibrate the GQS 40 at one of the plurality of locations based on the caparison of the first fuel data 110 received from the plurality of locations near the geographic location of the miscalibrated GQS 40, etc.) and/or the QGS miscalibration value. Automatic remote calibration may facilitate operating the engine systems 10 at optimal performance since the feed forward control may be provided with greater accuracy such that the engine controllers 100 operate the engines 60 according to the true or substantially true fuel composition of the fuel 22. In other embodiments, the fuel sensor calibration circuit 257 may provide a notification to a user on the user I/O device 240 that the GQS 40 may need to be calibrated (e.g., on-site calibration, a user may need to authorize the remote calibration, etc.).

According to another embodiment, the fuel sensor calibration circuit 257 is structured to compare a history of the fuel composition at a respective location to the first fuel data 110 received from one of the GQSs 40 located at the respective location (e.g., compare the fuel composition to the history of a respective fuel source 20 of a respective engine system 10, etc.). The fuel sensor calibration circuit 257 may be further structured to determine that the GQS 40 requires calibration based on the first fuel data 110 falling outside of a historically defined range of fuel compositions of the fuel 22 coming from the fuel source 20 of the engine system 10. The fuel sensor calibration circuit 257 may be further structured to remotely calibrate the miscalibrated GQS 40 based on the history of the first fuel data 110.

According to yet another embodiment, the fuel sensor calibration circuit 257 is structured to compare the first fuel data 110 received from a GQS 40 and the second fuel data 112 received from an ONGA 50 of a respective engine system 10. The fuel sensor calibration circuit 257 may be further structured to determine that the GQS 40 is miscalibrated based on the first fuel data 110 and the second fuel data 112 differing more than a threshold amount (e.g., more than a percentage difference, a magnitude difference, etc.). The fuel sensor calibration circuit 257 may be further structured to remotely calibrate the miscalibrated GQS 40 based on the second fuel data 112 received from the ONGA 50 of the same engine system 10 (e.g., in response to the first fuel data 110 differing from the second fuel data 112 by a more than the threshold amount, etc.). In other embodiments, the fuel sensor calibration circuit 257 may be further structured to additionally or alternatively calibrate the GQS 40 based on the first fuel data 110 received from other GQSs 40 within a geographical range/area of the location of the miscalibrated GQS 40, as described above (e.g., the second fuel data 112 may be used to determine that the GQS 40 is miscalibrated and not for calibration purposes, etc.).

According to still another embodiment, the fuel sensor calibration circuit 257 is structured to determine that the GQS 40 is miscalibrated based on the engine operation data 114 received from the engine controllers 100 of a respective engine system 10. For example, if the first fuel data 110 indicates a fuel composition of the fuel 22 and the engine controllers 100 operate the engines 60 according to that fuel composition and the engine operation data 114 indicates that the engines 60 are not operating properly, the feed forward control facilitated by the GQS 40 may be at fault. The fuel sensor calibration circuit 257 may thereby calibrate the GQS 40 based on the first fuel data 110 of surrounding GQSs 40 (e.g., within the geographical area of the miscalibrated GQS 40, etc.), the history of the first fuel data 110 at the respective location of the miscalibrated GQS 40, and/or the second fuel data 112 from the ONGA 50 at the respective location of the miscalibrated GQS 40 in response to the engine operation data 114 indicating poor performance of the engine 60. The above examples may similarly apply for the ONGAs 50 as described above in regards to the GQSs 40. Further, the use of the terms "calibrate" and "miscalibrated" are to be considered broad as demonstrated by the various aforementioned examples.

According to one embodiment, the fuel sensor calibration circuit 257 may include communication circuitry structured to facilitate the exchange of information, data, values, non-transient signals, etc. between and among the fuel sensor calibration circuit 257, the aggregation circuit 255, the engine systems 10 (e.g., the GQSs 40, the ONGAs 50, etc.), and/or the user I/O device 240. For example, the communication circuitry may include a channel comprising any type of communication channel (e.g., fiber optics, wired, wireless, etc.), wherein the channel may include any additional component for signal enhancement, modulation, demodulation, filtering, and the like. In this regard, the fuel sensor calibration circuit 257 may include communication circuitry including, but not limited to, wired and wireless communication protocols to facilitate reception of the first fuel data 110, the second fuel data 112, and/or the engine operation data 114 and to transmit calibration commands to the GQSs 40 and/or the ONGAs 50.

The fuel trend circuit 258 may be structured to receive the first fuel data 110 and/or the second fuel data 112 to monitor characteristics of the fuel composition of the fuel 22 across each of the respective geographic locations. For example, the fuel trend circuit 258 may be structured to interpret (e.g., analyze, etc.) the first fuel data 110 and/or the second fuel data 112 to monitor characteristics of the fuel composition across each of the respective geographic locations to determine fuel quality trends. Therefore, the fuel trend circuit 258 may be structured to facilitate monitoring the variability in the fuel composition across each of the engine systems 10 associated with the wireless sensor network (e.g., for display on the user I/O device 240, etc.). In another example, the fuel trend circuit 258 may facilitate monitoring trends including a rate of change and a magnitude of change in the fuel composition over time for each of the engine systems 10 at each geographic location. Such monitoring of trends across the engine systems 10 variously located at respective geographic locations may minimize or eliminate the need for manually surveying fuel sites (e.g., especially in remote areas, etc.), reducing both time investments and financial investments.

According to one embodiment, the fuel trend circuit 258 may include communication circuitry structured to facilitate the exchange of information, data, values, non-transient signals, etc. between and among the fuel trend circuit 258, the aggregation circuit 255, the engine systems 10 (e.g., the GQSs 40, the ONGAs 50, etc.), and/or the user I/O device 240. For example, the communication circuitry may include a channel comprising any type of communication channel (e.g., fiber optics, wired, wireless, etc.), wherein the channel may include any additional component for signal enhancement, modulation, demodulation, filtering, and the like. In this regard, the fuel trend circuit 258 may include communication circuitry including, but not limited to, wired and wireless communication protocols to facilitate reception of the first fuel data 110 and/or the second fuel data 112 and to transmit information to the user I/O device 240.

Figure 5:
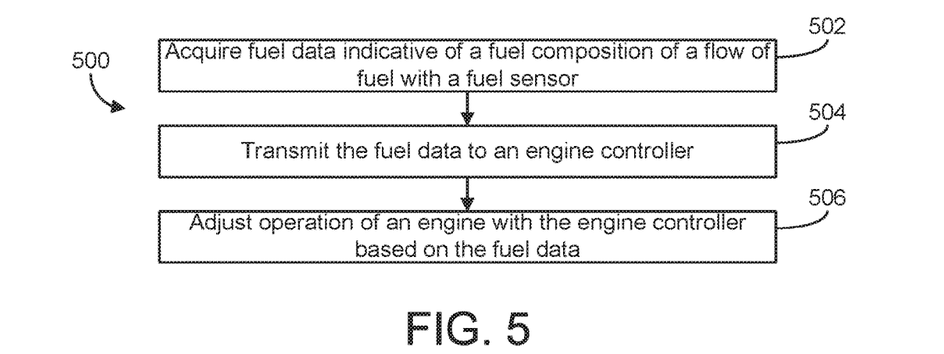
FIG. 5 is a flow diagram of a method for adaptively controlling an engine based on fuel quality, according to an example embodiment.

Referring now to FIG. 5, a method 500 for adaptively controlling an engine based on fuel quality is shown according to an example embodiment. Method 500 may be implemented with the engine 10 of FIG. 1 and the engine controller 100 of FIGS. 1-2. Accordingly, method 500 may be described with regards to FIGS. 1-2.

At step 502, a fuel sensor (e.g., the GQS 40, etc.) is positioned to acquire fuel data indicative of a fuel composition of a flow of fuel (e.g., the fuel 22, etc.). The fuel sensor may be positioned along a fuel conduit (e.g., the fuel line 30, etc.) between a fuel source (e.g., the fuel source 20, etc.) and one or more engines (e.g., the engines 60, etc.). The fuel source may include a tank or reservoir structured to hold the fuel, or a well head containing the fuel. The fuel may include natural gas, gasoline, diesel, propane, hydrogen, or still another fuel used in an internal combustion engine. The flow of fuel may be provided to the one or more engines for combustion to power another system (e.g., a power generation system, a vehicle, etc.). At step 504, the fuel sensor is structured to transmit the fuel data to an engine controller (e.g., the engine controller 100, etc.) of each of the one or more engines. The engine controller may interpret the fuel data to identify fluctuations or abnormalities in the fuel composition that may affect the performance of the respective engine the engine controller is communicably and operatively coupled to. At step 506, the engine controller of each of the one or more engines is structured to adjust an operating characteristic of the respective engine based on the fuel data. The operating characteristic may include an ignition timing, an injection timing, and/or an engine speed, among other possibilities. Adjusting the operating characteristic of the engine may prevent engine knock, engine shutdown, and/or engine damage by compensating for the fluctuations in the fuel composition to facilitate providing target combustion characteristics for optimum operation of the engine.

Figure 6:
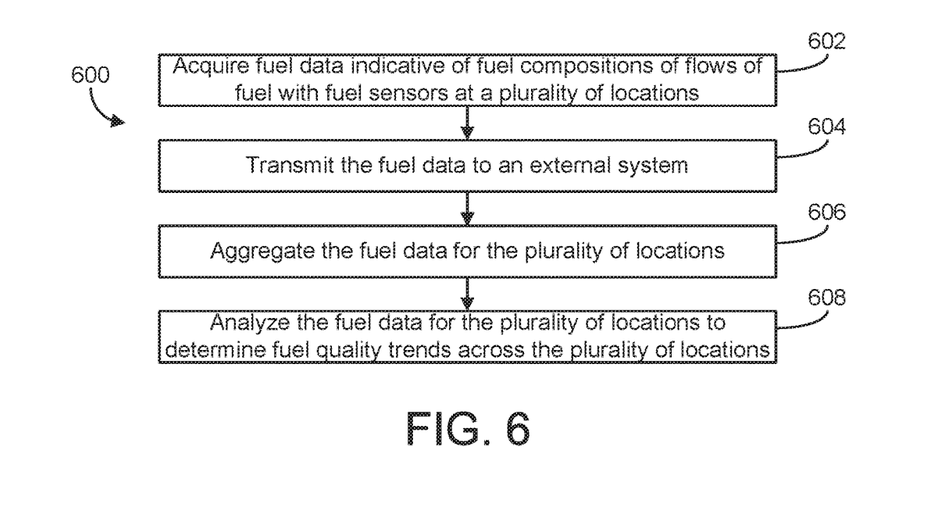
FIG. 6 is a flow diagram of a method for determining fuel quality trends, according to an example embodiment.

Referring now to FIG. 6, a method 600 for determining fuel quality trends is shown according to an example embodiment. Method 600 may be implemented with the engine system 10 of FIG. 1, the monitoring system 200 of FIG. 3, and/or the global analytics system 250 of FIGS. 3-4. Accordingly, method 600 may be described with regards to FIGS. 1 and 3-4.

At step 602, a sensor network including a plurality of fuel sensors (e.g., the GQSs 40, the ONGAs 50, etc.) are structured to acquire fuel data indicative of a fuel composition of a flow of fuel (e.g., the fuel 22, etc.) at a plurality of locations (e.g., each fuel sensor is associated with an individual engine system 10, etc.). The plurality of fuel sensors may each be positioned along a fuel conduit (e.g., the fuel line 30, a main fuel line, a pipeline, etc.) between a fuel source (e.g., the fuel source 20, etc.) and one or more engines (e.g., the engines 60, etc.). The fuel source may include a tank or reservoir structured to hold the fuel, or a well head containing the fuel. The fuel may include natural gas, gasoline, diesel, propane, hydrogen, or still another fuel used in an internal combustion engine. The flow of fuel may be provided to the one or more engines for combustion to power another system (e.g., a power generation system, a vehicle, etc.). At step 604, at least one of the plurality of fuel sensors of the sensor network are structured to transmit the fuel data to an external system (e.g., the global analytics system 250, etc.) over a network (e.g., the network 210, etc.).

At step 606, the external system is structured to aggregate the fuel data received from each of the fuel sensors at the various geographic locations. At step 608, the external system is structured to interpret (e.g., analyze, etc.) the fuel data to monitor characteristics of the fuel composition across each of the respective geographic locations to determine fuel quality trends (e.g., perform a fuel survey, etc.). For example, the external system may be used to monitor variability in the fuel composition across the engine systems associated with the wireless sensor network. In another example, the external system may be used to monitor trends including a rate of change and a magnitude of change in the fuel composition over time for each of the engine systems at each geographic location.

Figure 7:
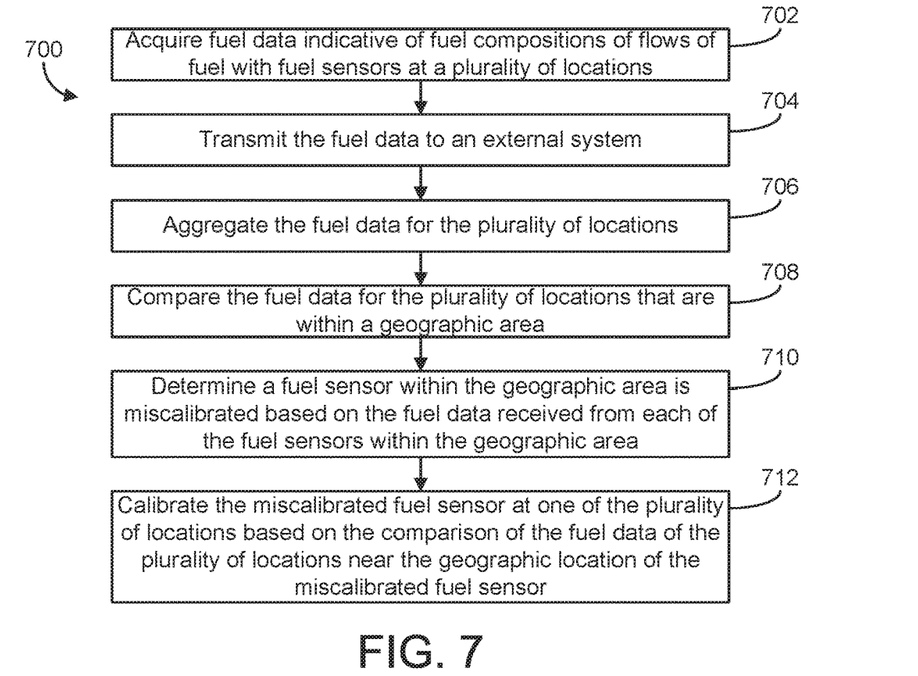
FIG. 7 is a flow diagram of a method for calibrating a fuel sensor, according to an example embodiment.

Referring now to FIG. 7, a method 700 for calibrating a fuel sensor is shown according to an example embodiment. Method 700 may be implemented with the engine system 10 of FIG. 1, the monitoring system 200 of FIG. 3, and/or the global analytics system 250 of FIGS. 3-4. Accordingly, method 700 may be described with regards to FIGS. 1 and 3-4.

At step 702, a sensor network including a plurality of fuel sensors (e.g., the GQSs 40, the ONGAs 50, etc.) is structured to acquire fuel data indicative of a fuel composition of a flow of fuel (e.g., the fuel 22, etc.) at a plurality of locations (e.g., each fuel sensor is associated with an individual engine system 10, etc.). The plurality of fuel sensors may each be positioned along a fuel conduit (e.g., the fuel line 30, etc.) between a fuel source (e.g., the fuel source 20, etc.) and one or more engines (e.g., the engines 60, etc.). The fuel source may include a tank or reservoir structured to hold the fuel, or a well head containing the fuel. The fuel may include natural gas, gasoline, diesel, propane, hydrogen, or still another fuel used in an internal combustion engine. The flow of fuel may be provided to the one or more engines for combustion to power another system (e.g., a power generation system, a vehicle, etc.). At step 704, at least one of the plurality of fuel sensors of the sensor network is structured to transmit the fuel data to an external system (e.g., the global analytics system 250, etc.) over a network (e.g., the network 210, etc.).

At step 706, the external system is structured to aggregate the fuel data received from each of the fuel sensors at the various geographic locations. At step 708, the external system is structured to compare the fuel data received from each of the plurality of fuel sensors within a geographic area (e.g., within a one, five, ten, fifty, etc. mile radius of each other, etc.). At step 710, the external system is structured to determine at least one of the fuel sensors within the geographic area is miscalibrated based on the fuel data received from each of the plurality of fuel sensors within the geographic area (e.g., by determining a miscalibration value based on the fuel data, etc.). At step 712, the external system is structured to remotely calibrate the miscalibrated fuel sensor based on the fuel data received from each of the plurality of fuel sensors (and/or the miscalibration value) within the geographic area of the miscalibrated fuel sensor (e.g., calibrate the fuel sensor at one of the plurality of locations based on the caparison of the fuel data from the plurality of locations near the geographic location of the miscalibrated fuel sensor, etc.).

Figure 8:
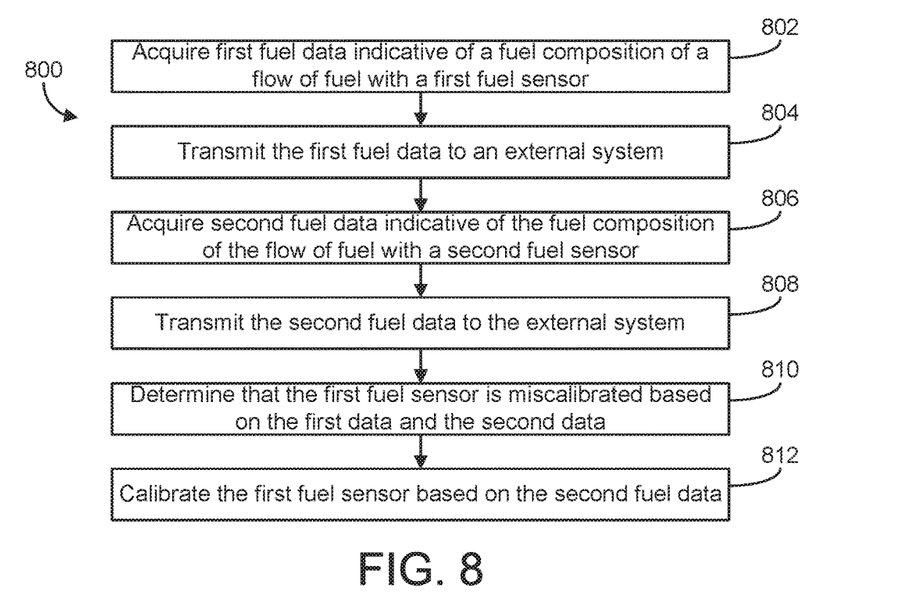
FIG. 8 is a flow diagram of a method for calibrating a fuel sensor, according to another example embodiment.

Referring now to FIG. 8, a method 800 for calibrating a fuel sensor is shown according to another example embodiment. Method 800 may be implemented with the engine system 10 of FIG. 1, the monitoring system 200 of FIG. 3, and/or the global analytics system 250 of FIGS. 3-4. Accordingly, method 800 may be described with regards to FIGS. 1 and 3-4.

At step 802, a first fuel sensor (e.g., the GQS 40, etc.) is positioned to acquire first fuel data indicative of a fuel composition of a flow of fuel (e.g., the fuel 22, etc.). The first fuel sensor may be positioned along a fuel conduit (e.g., the fuel line 30, etc.) between a fuel source (e.g., the fuel source 20, etc.) and one or more engines (e.g., the engines 60, etc.). The fuel source may include a tank or reservoir structured to hold the fuel, or a well head containing the fuel. The fuel may include natural gas, gasoline, diesel, propane, hydrogen, or still another fuel used in an internal combustion engine. The flow of fuel may be provided to the one or more engines for combustion to power another system (e.g., a power generation system, a vehicle, etc.). At step 804, the first fuel sensor is structured to transmit the first fuel data to an external system (e.g., the global analytics system 250, etc.) over a network (e.g., the network 210, etc.).

At step 806, a second fuel sensor (e.g., the ONGA 50, etc.) is positioned to acquire second fuel data indicative of the fuel composition of the flow of fuel. The second fuel sensor may be positioned along the fuel conduit upstream or downstream of the first fuel sensor. At step 808, the second fuel sensor is structured to transmit the second fuel data to the external system over the network. In other embodiments, the first sensor and/or the second sensor are communicably coupled to a communications system (e.g., the communications circuit 107, etc.) that facilitates transmitting the first fuel data and/or the second fuel data to the external system.

At step 810, the external system is structured to determine that the first fuel sensor is miscalibrated based on the first fuel data and the second fuel data. At step 812, the external system is structured to remotely calibrate the miscalibrated first fuel sensor based on the second fuel data (e.g., in response to the first fuel data differing from the second fuel data by a more than threshold amount such as a percentage difference, a magnitude difference, etc.). In other embodiments, the external system is structured to additionally or alternatively calibrate the first fuel sensor based on fuel data received from other fuel sensors within a geographical range/area of the location of the miscalibrated first fuel sensor (e.g., see steps 708-712 of method 700, rather than based on the second fuel data, the second fuel data may be used to determine that the first fuel sensor is miscalibrated, etc.).

It should be understood that no claim element herein is to be construed under the provisions of 35 U.S.C. § 112(f), unless the element is expressly recited using the phrase "means for." The schematic flow chart diagrams and method schematic diagrams described above are generally set forth as logical flow chart diagrams. As such, the depicted order and labeled steps are indicative of representative embodiments. Other steps, orderings and methods may be conceived that are equivalent in function, logic, or effect to one or more steps, or portions thereof, of the methods illustrated in the schematic diagrams. Further, reference throughout this specification to "one embodiment", "an embodiment", "an example embodiment", or similar language means that a particular feature, structure, or characteristic described in connection with the embodiment is included in at least one embodiment of the present invention. Thus, appearances of the phrases "in one embodiment", "in an embodiment", "in an example embodiment", and similar language throughout this specification may, but do not necessarily, all refer to the same embodiment.

Additionally, the format and symbols employed are provided to explain the logical steps of the schematic diagrams and are understood not to limit the scope of the methods illustrated by the diagrams. Although various arrow types and line types may be employed in the schematic diagrams, they are understood not to limit the scope of the corresponding methods. Indeed, some arrows or other connectors may be used to indicate only the logical flow of a method. For instance, an arrow may indicate a waiting or monitoring period of unspecified duration between enumerated steps of a depicted method. Additionally, the order in which a particular method occurs may or may not strictly adhere to the order of the corresponding steps shown. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

Many of the functional units described in this specification have been labeled as circuits, in order to more particularly emphasize their implementation independence. For example, a circuit may be implemented as a hardware circuit comprising custom very-large-scale integration (VLSI) circuits or gate arrays, off-the-shelf semiconductors such as logic chips, transistors, or other discrete components. A circuit may also be implemented in programmable hardware devices such as field programmable gate arrays, programmable array logic, programmable logic devices or the like.

As mentioned above, circuits may also be implemented in machine-readable medium for execution by various types of processors, such as processor 102 of FIG. 2. An identified circuit of executable code may, for instance, comprise one or more physical or logical blocks of computer instructions, which may, for instance, be organized as an object, procedure, or function. Nevertheless, the executables of an identified circuit need not be physically located together, but may comprise disparate instructions stored in different locations which, when joined logically together, comprise the circuit and achieve the stated purpose for the circuit. Indeed, a circuit of computer readable program code may be a single instruction, or many instructions, and may even be distributed over several different code segments, among different programs, and across several memory devices. Similarly, operational data may be identified and illustrated herein within circuits, and may be embodied in any suitable form and organized within any suitable type of data structure. The operational data may be collected as a single data set, or may be distributed over different locations including over different storage devices, and may exist, at least partially, merely as electronic signals on a system or network.

The computer readable medium (also referred to herein as machine-readable media or machine-readable content) may be a tangible computer readable storage medium storing the computer readable program code. The computer readable storage medium may be, for example, but not limited to, an electronic, magnetic, optical, electromagnetic, infrared, holographic, micromechanical, or semiconductor system, apparatus, or device, or any suitable combination of the foregoing. As alluded to above, examples of the computer readable storage medium may include but are not limited to a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), an optical storage device, a magnetic storage device, a holographic storage medium, a micromechanical storage device, or any suitable combination of the foregoing. In the context of this document, a computer readable storage medium may be any tangible medium that can contain, and/or store computer readable program code for use by and/or in connection with an instruction execution system, apparatus, or device.

The computer readable medium may also be a computer readable signal medium. A computer readable signal medium may include a propagated data signal with computer readable program code embodied therein, for example, in baseband or as part of a carrier wave. Such a propagated signal may take any of a variety of forms, including, but not limited to, electrical, electro-magnetic, magnetic, optical, or any suitable combination thereof. A computer readable signal medium may be any computer readable medium that is not a computer readable storage medium and that can communicate, propagate, or transport computer readable program code for use by or in connection with an instruction execution system, apparatus, or device. As also alluded to above, computer readable program code embodied on a computer readable signal medium may be transmitted using any appropriate medium, including but not limited to wireless, wireline, optical fiber cable, Radio Frequency (RF), or the like, or any suitable combination of the foregoing. In one embodiment, the computer readable medium may comprise a combination of one or more computer readable storage mediums and one or more computer readable signal mediums. For example, computer readable program code may be both propagated as an electro-magnetic signal through a fiber optic cable for execution by a processor and stored on RAM storage device for execution by the processor.

Computer readable program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The computer readable program code may execute entirely on the user's computer (such as via the engine controller 100 of FIGS. 1-2), partly on the user's computer, as a stand-alone computer-readable package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The program code may also be stored in a computer readable medium that can direct a computer, other programmable data processing apparatus, or other devices to function in a particular manner, such that the instructions stored in the computer readable medium produce an article of manufacture including instructions which implement the function/act specified in the schematic flowchart diagrams and/or schematic block diagrams block or blocks.

Accordingly, the present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. An apparatus, comprising:
    an aggregation circuit structured to interpret fuel data acquired by a plurality of gas quality sensors, the fuel data indicative of a fuel composition of a fuel, each of the plurality of gas quality sensors associated with a different engine system, each respective engine system positioned at a different geographic location having a fuel source that provides the fuel; and
    a calibration circuit structured to:
        compare the fuel data received from a subset of the plurality of gas quality sensors located within a select geographic area;
        determine a gas quality sensor miscalibration value for the subset of the plurality of gas quality sensors based on the fuel data received from the subset of the plurality of gas quality sensors within the select geographic area; and remotely calibrate a miscalibrated gas quality sensor of the subset of the plurality of gas quality sensors based on the gas quality sensor miscalibration value.

2. The apparatus of claim 1, wherein the plurality of gas quality sensors include an optical sensor, wherein the optical sensor includes at least one of a non-dispersive infrared optical sensor and a tunable diode laser optical sensor.

3. The apparatus of claim 1, wherein the fuel includes natural gas provided by a well head containing the natural gas.

4. The apparatus of claim 1, wherein each of the plurality of gas quality sensors are positioned upstream of an engine test cell center having at least one engine and downstream of the fuel source.

5. The apparatus of claim 1, further comprising a trend circuit structured to interpret the fuel data to monitor characteristics of the fuel composition across each of the different geographic locations.

6. The apparatus of claim 5, wherein the characteristics of the fuel composition include at least one of a rate of change in the fuel composition at each different geographic location, a magnitude of change in the fuel composition at each different geographic location, and a variability of fuel composition across the different geographic locations.

7. A method, comprising:
aggregating fuel data received from a plurality of fuel sensors, the fuel data indicative of a fuel composition of a fuel, each of the plurality of fuel sensors associated with a different engine system, each respective engine system positioned at a different geographic location having a fuel source that provides the fuel;
comparing the fuel data received from a subset of the plurality of fuel sensors located within a select geographic area;
determining a fuel sensor miscalibration value for the subset of the plurality of gas quality sensors based on the fuel data received from the subset of the plurality of fuel sensors located within the select geographic area; and
remotely calibrating a miscalibrated fuel sensor of the subset of the plurality of fuel sensors based on the fuel sensor miscalibration value.

8. The method of claim 7, further comprising interpreting the fuel data to monitor characteristics of the fuel composition across each of the different geographic locations.

9. The method of claim 7, wherein the plurality of fuel sensors include an optical sensor, wherein the optical sensor includes at least one of a non-dispersive infrared optical sensor and a tunable diode laser optical sensor.

10. The method of claim 7, wherein the fuel includes natural gas provided by a well head containing the natural gas.

11. A system, comprising:
a wireless sensor network including at least:
a first gas sensor associated with a first engine system located at a first geographic location, the first gas sensor positioned to acquire first fuel data indicative of a first fuel composition of a fuel provided by a first fuel source to a first engine of the first engine system;
a second gas sensor associated with a second engine system located at a second geographic location, the second gas sensor positioned to acquire second fuel data indicative of a second fuel composition of the fuel provided by a second fuel source to a second engine of the second engine system; and
a third gas sensor associated with a third engine system located at a third geographic location, the third gas sensor positioned to acquire third fuel data indicative of a third fuel composition of the fuel provided by a third fuel source to a third engine of the third engine system; and
an external monitoring system structured to:
receive the first fuel data, the second fuel data, and the third fuel data from the first gas sensor, the second gas sensor, and the third gas sensor, respectively;
determine that one of the first gas sensor, the second gas sensor, or the third gas sensor is miscalibrated based on the first fuel data, the second fuel data, and the third fuel data; and
remotely calibrate the one of the first gas sensor, the second gas sensor, or the third gas sensor that is miscalibrated.

12. The system of claim 11, wherein at least one of the first engine system, the second engine system, or the third engine system includes an online natural gas analyzer structured to acquire fourth fuel data indicative of the fuel composition of the fuel.

13. The system of claim 12, wherein the external monitoring system is structured to determine that one of the first gas sensor, the second gas sensor, or the third gas sensor is miscalibrated based on (i) at least one of the first fuel data, the second fuel data, or the third fuel data and (ii) the fourth fuel data.

14. The system of claim 13, wherein the external monitoring system is structured to remotely calibrate the one of the first gas sensor, the second gas sensor, or the third gas sensor based on the fourth fuel data.

15. The system of claim 11, wherein the external monitoring system is structured to determine that one of the first gas sensor, the second gas sensor, or the third gas sensor is miscalibrated by comparing the first fuel data, the second fuel data, and the third fuel data in response to the first geographic location, the second geographic location, and the third geographic location being within a select geographic area.

16. The system of claim 15, wherein the external monitoring system is structured to remotely calibrate the one of the first gas sensor, the second gas sensor, or the third gas sensor based on the the first fuel data, the second fuel data, and the third fuel data.

17. The system of claim 11, wherein the external monitoring system is further structured to aggregate fuel data from a plurality of gas quality sensors to at least one of (i) monitor variability in the fuel composition across engine systems associated with the wireless sensor network and (ii) monitor trends including a rate of change and a magnitude of change in the fuel composition over time for each of the engine systems.

18. The system of claim 11, wherein at least one of the first gas sensor, the second gas sensor, or the third gas sensor includes an optical sensor.

19. The system of claim 18, wherein the optical sensor includes at least one of a non-dispersive infrared optical sensor and a tunable diode laser optical sensor.

20. The system of claim 11, wherein the first fuel source, the second fuel source, and the third fuel source are connected to a central fuel source.

* * * * *